United States Patent [19]

Schneider et al.

[11] Patent Number: 4,546,436

[45] Date of Patent: Oct. 8, 1985

[54] PORTABLE PH DATA COLLECTOR

[75] Inventors: Wolfger Schneider, Columbia; Richard J. Johns, Baltimore, both of Md.

[73] Assignee: The Johns Hopkins University, Baltimore, Md.

[21] Appl. No.: 511,383

[22] Filed: Jul. 6, 1983

[51] Int. Cl.[4] .............................................. G06F 15/42
[52] U.S. Cl. ................... 364/415; 364/417; 346/33 ME
[58] Field of Search ........................ 364/415, 417, 413; 346/33 ME; 128/635, 710, 631; 324/438

[56] References Cited

U.S. PATENT DOCUMENTS

| 4,109,527 | 8/1978 | Goode, Jr. .................. 374/142 X |
| 4,326,535 | 4/1982 | Steffel et al. ..................... 128/631 |
| 4,346,718 | 8/1982 | Morris ............................. 128/710 |
| 4,384,586 | 5/1983 | Christiansen ..................... 128/635 |

OTHER PUBLICATIONS

A Microprocessor-Based ECG Monitor for Ambulatory Patients: Moody et al., Eighth NE Bioengineering Conference 3/27-28/1980.
Continuous Recording of Human Cerebral Blood How & Metabolism: Gotoh et al., Med. Res. Eng., 1966.
Flexible pH Electrode, Microelectrodes Inc., 1975.
Long Term Recording & Computer Analysis of Simultaneous Gastric and Duodenal pH Under Normal Conditions in Man: McCoy et al., Clinical Physical, 1980.

*Primary Examiner*—Jerry Smith
*Assistant Examiner*—Louis Woo
*Attorney, Agent, or Firm*—Robert E. Archibald; Howard W. Califano

[57] ABSTRACT

The present invention provides an apparatus for continuously recording physiological data. The invention includes a unique data mapping and compression technique which allows relatively long term data acquisition without compromising the data sampling rate. The present physiological data recorder has application in recording physiological data which is non-periodic and is characterized by "bursts" of rapid activity interspersed among relatively long periods during which there is little or no activity. The invention has specific application in recording pH data in ambulatory patients and comprises a unique data compression means, an automatic calibration means, and a digital or analogue data playback means.

26 Claims, 13 Drawing Figures

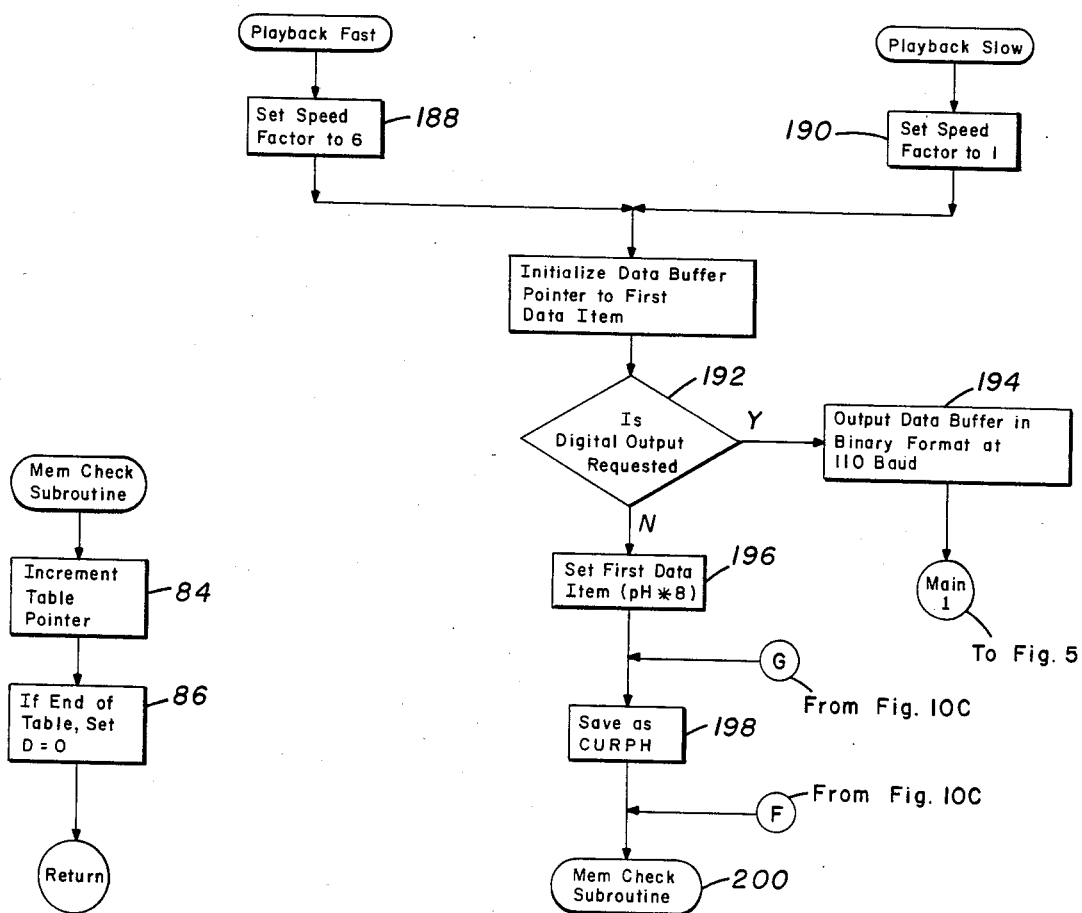
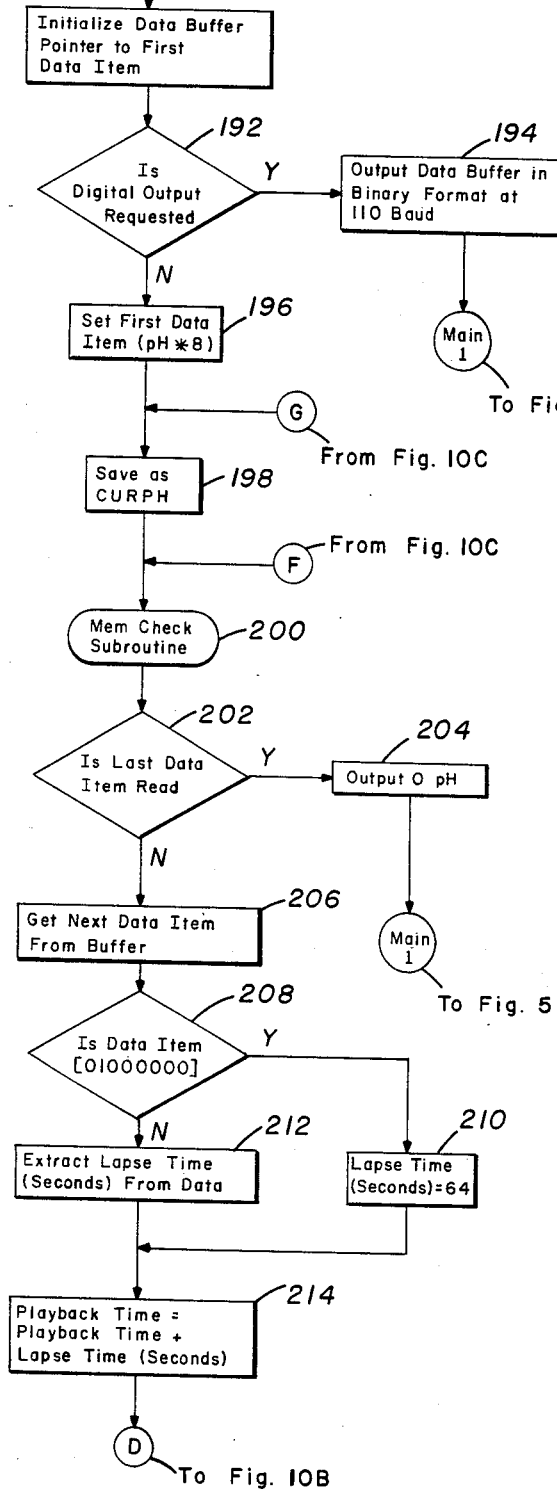
FIG. 9
FIG. 10A

PORTABLE PH DATA COLLECTOR

BACKGROUND AND/OR ENVIRONMENT OF THE INVENTION

1. Field of the Invention

The invention relates to an apparatus for continuously recording physiological data in ambulatory patients. More particularly, the invention teaches a physiological data recorder having a unique data compression means, an automatic calibration means, and a digital or analogue data playback means.

2. Description of the Contemporary and/or Prior Art

Gastroesophageal reflux disease (GERD) is a common clinical disorder in which esophageal irritation by regurgitated gastric contents produce symptoms and esophageal inflamation. Classical symptoms of heartburn and oral regurgitation of a sour or bitter liquid permit a reasonably reliable diagnosis without the need to resort to laboratory tests. However, GERD can occur with a large array of atypical symptoms that can mimic pulmonary, cardiac, biliary and non-esophageal peptic disease. With these atypical symptoms, laboratory evaluation for evidence of GERD is often necessary.

Unfortunately, currently applied clinical laboratory tests for the diagnosis of GERD are either too insensitive or too non-specific. For example, the traditional barium swallow study documents only about 40% of the refluxers while the acid perfusion test (the Bernstein test) is positive in as many as 10% of normal individuals and 40% of those with non-esophageal peptic disorders.

Over the past decade, continuous pH monitoring has been used to generate better information on GERD. A pH probe is placed via the nose into the esophageal lumen and the patient is allowed normal activity and ingestion of food. Intraesophageal pH is monitored through the recording period which usually ranges from 14 to 24 hours in duration. The aim is to provide a representative sample of both daytime and nighttime reflux activity under near physiologic conditions.

Many authorities consider the continuous pH monitor to be the best single test for the diagnosis of GERD. In addition, it provides valuable information on the pathogenesis of reflux and is the first test to provide meaningful information on the effect of therapy on the severity of reflux. However, prior art devices for continuously monitoring pH in ambulatory patients are inadequate.

Typical physiological data recorders which are useful with ambulatory patients fall into two general categories. The first category includes physiological data recorders which collect and record physiological data which are periodic in nature and have a recognizable waveform. Electrocardiagram recorders are typical of this category and look for irregularities in the EKG waveform before recording immediately proceeding or following signals. U.S. Pat. Nos. 3,755,783 and 4,250,888 are typical physiological recorders which analyze irregularities in repetitive biological processes.

The second category includes physiological data recorders which record a physiological phenomenon which is not a repetitive biological process. This category requires an extremely large data storage capacity since there is no simple function which allows normal performance to be distinguished from abnormal performance. Continuously recording intraesophageal pH falls into the second category. The episodic nature of the gastroesophageal reflux behavior is not a repetitive biological process with a clearly recognizable pattern.

Prior art physiological recorders which monitor non-periodic occurrences either require a large data storage capacity or are required to transmit the data to a remote site for recording. A blood pressure monitor for ambulatory patients invented by V. David Squires et al (U.S. Pat. No. 4,216,776) records data on a continuously-running portable tape recorder. This method can only record continuous data for a limited amount of time and might, because of its potential size, inhibit the normal movement of an ambulatory patient. U.S. Pat. No. 4,326,535 to Charles H. Steffel et al entitled "Circuit and Method for the Radio Telemetry of Esophageal pH in an ECG Radio Telemetry System" overcomes the data storage problem by transmitting pH values from the patient's unit to a remote site for recording. Although, the patient's unit can be reduced in size, the patient's activity is limited to the transmitter range. Accordingly, the range of patient activity in which pH levels can be monitored is limited.

SUMMARY OF THE INVENTION

The present inventors have invented a portable pH data collector incorporating a data compression and selection technique which is uniquely suited to record the episodic nature of the gastroesophageal reflux behavior. The data collection technique reduces the number of recorded data entries and also reduces the memory space necessitated for recording each data entry.

The invented pH data recorder is a microcomputer controlled device which operates in an auto calibration phase, a data acquisition and recording phase, and a playback- phase. During the auto calibration phase, the pH probe is calibrated for a particular patient and a "calibration constant" is calculated which will subsequently be used for automatically converting measured data into actual pH levels.

During the data acquisition and recording phase, data words are recorded for each "event". An "event" occurs when the patient has actuated an "event marker" or when there is an incremental change in the measured pH level. The patient will actuate an "event marker" by pressing a key on the unit's keypad, when a relevant physiological symptom or other event such as eating occurs. The measured pH level is digitized and scaled automatically in accordance with the "calibration constant" and rounded to an integer value. In the preferred embodiment, the device checks for the actuation of an "event marker" once every 1/10th second and checks for an incremental change in pH level once every second.

A compressed data record is recorded for each "event". Each compressed data record contains two components: (1) the time elapsed since the last recorded "event" or the last data entry; and, (2) a tag which indicates the type of "event". The tag indicates whether the "event" corresponds to: (1) the actuation of an "event marker", (2) an incremental increase in pH level; (3) an incremental decrease in pH, or (4) no event having occurred within a maximum elapsed time period. The maximum elapsed time period is chosen to reduce the number of bits required to store the time elapsed for each event. (If 6 bits of a data entry are allocated to elapsed time between "events", the maximum elapsed time period would be sixty-four seconds. If an "event" did not occur within sixty-four seconds a data entry is recorded and the clock is initialized). The invented data reduction and compression technique gathers continuous pH data which fluctuate as a function of time, and maps out and records time records as a function of "events". In other words, the present technique does the following data mapping operation to compress and reduce data records: $y(t) \rightarrow t(y)$; where, y=pH value and t=time elapsed.

The present data mapping and compression technique allows relatively long term data acquisition without compromising the data sampling rate. In the preferred embodiment, the data collection unit can maintain a data resolution of one entry per second during an event "burst" and still accommodate 24 hours worth of data. This technique has generalized application in recording physiological data which is "bursty" are non-periodic in nature. Such physiological data are characterized by bursts of rapid activity interspersed among relatively long periods of quiescence or low levels of activity.

By way of example, in the preferred embodiment an 8-bit data word is used with 6 bits allocated to record elapsed time and 2 bits allocated to record an "event" tag. If neither an "event marker" is actuated nor an incremental change in the pH is detected after sixty-four seconds, the program records a [01000000] and reinitializes the elapsed time counter. If an "event marker" is detected the program will record [00XXXXXX] where the bits designated by the letter X represent the time elapsed from the last recorded entry. If an incremental change in pH is detected the device records [10XXXXXX] for an increase in pH or [11XXXXXX] for a decrease in pH, where bits designated by the letter X represent the elapsed time from the last recorded entry.

After the pH data have been recorded, the invented apparatus is operated in the playback phase and reconstructs the compressed data in an analog or digital format. The analog playback mode generates an output voltage which drives a standard medical strip chart recorder, or its equivalent. The strip chart will display the reconstructed data and show continuous pH changes as a function of time. The digital playback mode causes data entries stored in memory to be transferred at a 110 Baud rate through an RS-232 data transfer link to a computer, such as a personal computer. The personal computer may have a display monitor and/or a printer with text and graphic capabilities, and may have support software enabling the computer to tabulate data concerning the duration, pH level, etc., of each gastroesophageal episode.

A first novel feature is a portable data collector which includes a data acquisition and compression technique which reduces the number of data entries and minimizes the memory space required for each data entry, thereby allowing a portable data collection unit, worn by an ambulatory patient, to gather up to 24 hours of physiological data bursts without compromising the data sampling rate.

A second novel feature is a portable pH data collector which is microcomputer controlled and includes an auto calibration phase, a data acquisition and recording phase, and a playback phase.

A third novel feature is a portable data collector which compresses records by mapping actual pH values which change as a function of time, into time elapsed data records which are recorded as a function of the occurrence of "events".

A fourth novel feature is a portable pH data collector which records data words on the occurrence of "events". "Events" occur when a patient has actuated an "event marker" or when an incremental change of pH has occurred. Each data entry records elapsed time from the last recorded entry, and a tag to indicate the nature of the "event".

A fifth novel feature is a portable data collector which includes a playback phase which reconstructs the compressed data records in an analog or digital format. The analog playback mode generates an output voltage necessary to drive a standard medical strip chart recorder.

BRIEF DESCRIPTION OF THE DRAWINGS

FIG. 7B represents a continuation of FIG. 7A.

FIG. 9 is a flow chart illustrating the MEMCHECK subroutine.

FIGS. 10A, 10B and 10C contain a flow chart illustrating the PLAYBACK subroutine. FIGS. 10B and 10C are continuations of FIG. 10A.

DETAILED DESCRIPTION OF THE PREFERRED EMBODIMENT

Figure 1:
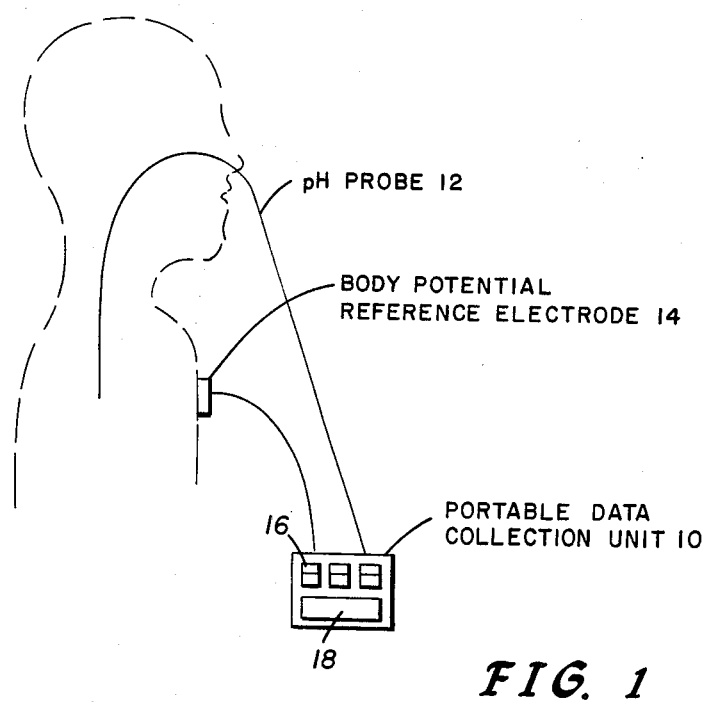
FIG. 1 a diagrammatic view of the invented portable pH data collector as used in the data acquisition and compression phase.

FIG. 1 illustrates the portable pH data collection apparatus for continuously recording the intraesophageal pH of an ambulatory patient. The invented apparatus, in the data collection phase, generally comprises: a portable data collector 10, which can be comfortably worn by the patient; a pH probe 12; and, a body potential reference electrode 14. The pH probe 12 which may be a 2 millimeter diameter glass electrode is usually inserted through the patient's nostril passage into the esophagus. The body potential reference electrode 14 may be any suitable electrode, such as the standard AgCl-type body electrode, for attachment to the patient's skin. The portable pH data collection apparatus can also accommodate pH electrodes which have the reference electrode combined with it. The portable data collection unit 10 is a microprocessor-based data collection unit implemented with low-power CMOS-type analogue and digital integrated circuits. The portable data collection unit 10 generally contains a 6-key functional keypad 16, and a single digit liquid crystal display 18 used for operator feedback. A unique data collection and compression means (to be discussed in detail later) enables the portable data collection unit to sample pH levels once every second and encode and store pH data in memory. During the data collection phase, any keypad entries are interpreted as "event markers" which are recorded and subsequently used to correlate current pH activity with sensations observed by the patient, or patient activities.

Figure 2:
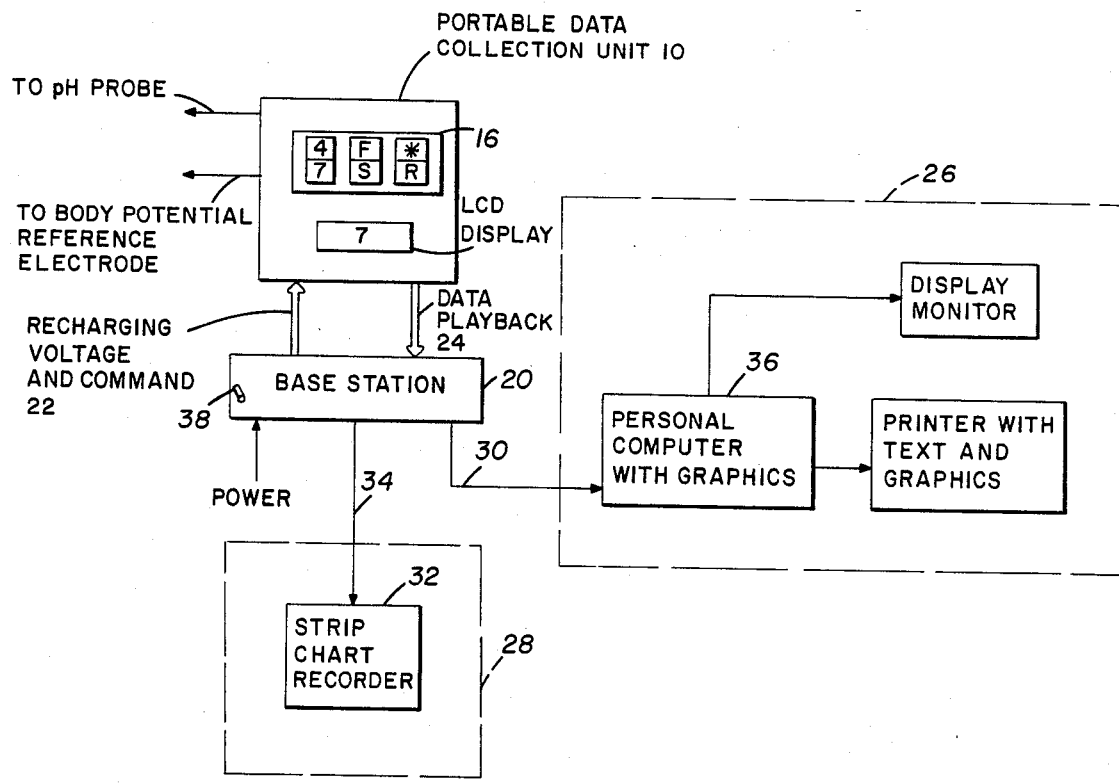
FIG. 2 is a diagrammatic view of the invented portable pH data collector connected in association with a base station during recharging and data playback phases.

FIG. 2 illustrates the portable data collection unit 10 connected in association with the base unit 20 during the battery recharge and data playback phase. The invented apparatus, in the recharge and data playback phase, generally comprises: a portable data collection unit 10, which has been disconnected from the pH probe 12 and the body potential reference electrode 14; a base station 20, which is electrically coupled to the portable data collection unit 10 via connectors 22 and 24 after the pH probe 12 and body potential reference electrode 14 have been disconnected; a digital playback means 26 connected to the base station 20 via a standard RS-232 data transferred link 30, or its equivalent; and, an optional analogue playback means 28, such as a standard medical strip chart recorder 32, connected to the base station via signal line 34. The base station 20 provides an electrical and mechanical interface for reading the data recorded by the portable data collection unit 10. A selection switch 38 on the base unit allows the operator to select between digital or analogue playback. Digital data are a straight binary dump of the portable data collection unit's memory and is sent via an RS-232 (DTE-type) interface at 110 Baud to any computing equipment, such as a personal computer 36. Data may also be reviewed on a strip chart recorder 32 at ten times or sixty times real time. The operator presses a sequence of keys on keypad 16 to select fast or slow playback.

The base station 20 is also used to recharge the batteries in the portable data collection unit 10. In the preferred embodiment, the portable data collection unit 10 contains rechargeable batteries which require 30 hours to recharge fully and will power the disconnected remote unit for up to 110 hours. Once the batteries are fully charged, four hours is required to restore the charge fully following a 24-hour period during which the portable data collection unit is disconnected from the base station. The batteries are automatically charged when the portable data collection unit is attached to the base station.

In operation, the invented apparatus consists of three basic phases, each of which may consist of one or two modes: (1) The calibration phase selects reference points which are subsequently used for converting voltage levels sensed on the pH probe 12 and body potential reference electrode 14 into pH levels; (2) The data collection phase records in memory the time elapsed between an incremental change in pH or the actuation of an "event marker"; and, (3) The data playback phase formats the collected data for display on a strip chart recorder or for transmission to a computer. The operator can select a fast or slow analogue playback mode by pressing the appropriate keys on the portable data collecting unit's keypad 16.

Figure 3:
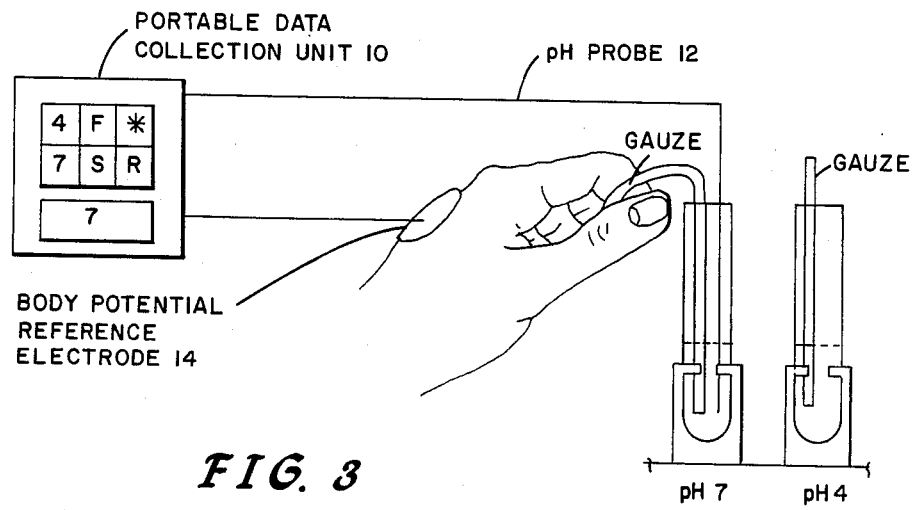
FIG. 3 is a diagrammatic view of the invented portable pH data collector as used in the calibration phase.

FIG. 3 illustrates the calibration phase for the invented portable data collection apparatus. During this phase, the body potential reference electrode 14 is attached to the body of the patient and the pH probe is first placed in a container holding a reference pH solution of pH 4 and then in a reference solution of pH 7. Each solution can be placed in a conductive container and held by the patient during calibration, or the patient can touch a soaked gauze extending from a test tube containing the reference pH solution. The portable data collection unit will be automatically calibrated by pressing the "4" button or the "7" button on the keypad 16 for solutions of pH 4 and pH 7, respectively. In the preferred embodiment, the enter key [*] is pressed to start the activity (i.e., automatic calibration in this case) selected by the previously actuated key.

Once calibrated and with the pH electrode in place, the portable data collection unit 10 can proceed to the data collection phase by pressing the record key [R] followed by the enter key [*]. Once in the data collection mode, the portable data collection unit will remain in that mode until disconnected from the pH probe and inserted into the base station. During the data collection phase, illustrated in FIG. 1, the pH probe continuously measures intraesophageal pH, and the actuation of any key on keypad 16 will be interpreted as an "event marker"-the patient will actuate an "event marker" upon observation of various sensations or other events.

During the data collection phase, pH values are measured by an ultra high input impedance amplifier and are digitized once per second, by an eight-bit analogue to digital converter. The digitized data are then suitably scaled by a microprocessor in accordance with the calibration points. The current pH digital value is then compared with the previously calculated digitized pH value and if a pH difference greater than one is detected, the time elapsed from the previous event is recorded. The relevant data are encoded and stored in a read/write memory. The applicants have found a 6K byte read/write memory to have an adequate memory capacity. The first stored data word records the initial measured pH value. All subsequent data bytes are stored upon the occurrence of one of the following four "events":

1. The current pH sample is one pH greater than the last pH sample.
2. The current pH sample is one pH smaller than the last pH sample.
3. The current pH sample is the same as the last 64 pH samples (i.e., the pH value has not changed in the last 64 seconds).
4. An "event marker" has been actuated.

These "events" and the time of occurrence since the last "event" are encoded in each byte of information as follows:

| Bit position |
| --- |
| 7 6 5 4 3 2 1 0 |
| [Tag] [Elapsed Time] |
| most significant digit / least significant digit |

| Tag | | identified event |
| --- | --- | --- |
| 0 | 0 | "event marker" pressed |
| 0 | 1 | no change in last sixty-four seconds |
| 1 | 0 | 1 pH decrement since last event |
| 1 | 1 | 1 pH increment since last event |

In the preferred embodiment only pH values of one through five are deemed medically important and only changes within this range are recorded. This novel data compression and selection technique is uniquely suited to record the episodic nature of the gastroesophageal reflux behavior.

The third, or data playback phase, is illustrated in Figure 2. The pH probe and the body potential reference electrode are disconnected from the portable data collection unit 10 and the portable unit is mechanically and electrically connected to the base station 20. In the preferred embodiment, the mechanical design is such that the patient electrodes must be disconnected from the portable data collection unit 10 before it can be connected to the a.c. line-powered base station 20. This provides electrical safety for the patient. A switch 38 on the base station allows the operator to switch between a digital playback mode or an analogue playback mode. In the digital playback mode, data bytes stored in the portable unit's read/write memory are transferred at a 110 baud rate through an RS-232 data transfer link to a computer, such as a personal computer 36. The personal computer 36 may have a display monitor and/or a printer with text and graphic capabilities, and may have support software enabling the computer to tabulate data concerning the duration, pH level, etc., of each gastroesophageal reflux episode. In the analogue mode, a signal is sent via line 34 to a strip chart recorder. In the preferred embodiment a strip chart having a zero through ten volt range is used with pH value related to input voltage as follows:

| | |
|---|---|
| end of data | 1V |
| 1 pH | 2V |
| 2 pH | 3V |
| 3 pH | 4V |
| 4 pH | 5V |
| 5 pH | 6V |
| >5 pH | 8V |
| "event marker" | 10V |

The data may be viewed on the strip chart at a rate of ten times or sixty times real time, by the operator pressing either the slow key [S] or fast key [F], respectively on keypad 16. The operator may choose to view the data initially at the fast rate and when an episode is noted the operator may press the slow key [S] for a presentation of the data. The fast or slow key can be pressed at any time during the data playback phase.

Figure 4:
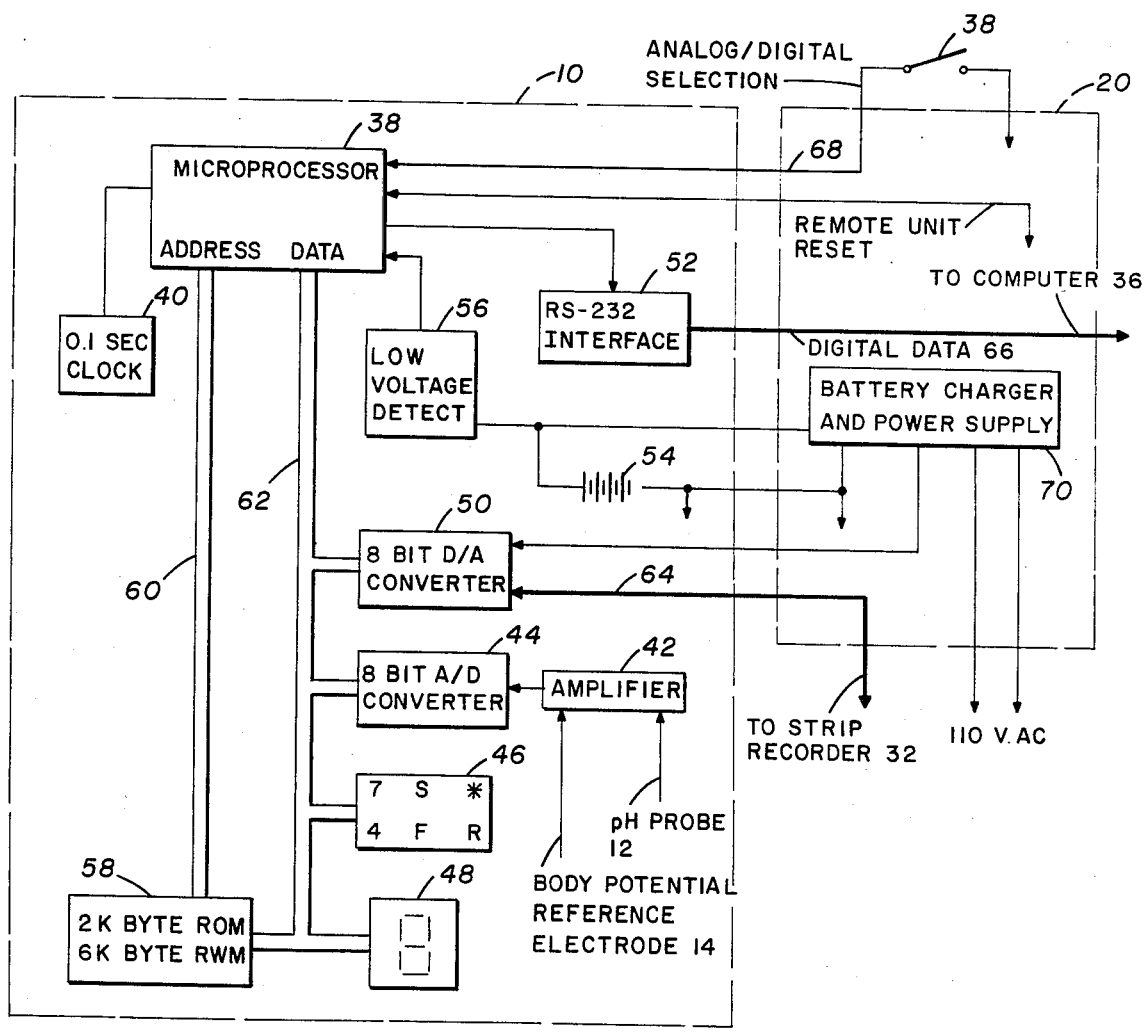
FIG. 4 is a block diagrammatic view of the invented portable pH data collector.

FIG. 4 is a block diagrammatic view of the analogue and digital circuits used in the portable data collection unit 10, and the base station 20. The portable data collection unit generally comprises: a microprocessor 38; a one-second clock 40; an ultra-high input impedance amplifier 42 which is connected to the pH probe 12 and the body potential reference electrode 14; an eight-bit analogue-to-digital converter 44; a six-key functional keypad 46; a single-digit liquid crystal display 48; an eight-bit digital-to-analogue converter 50 for supplying the analogue playback signal; an RS-232 interface 52 for supplying digital data to a remote personal computer; a rechargeable nickel cadmium battery 54; a low-voltage detector 56 for alerting the microprocessor 38 when there is a decrease in battery voltage; and a digital memory 58, which, in the preferred embodiment, is a 2K byte read only memory and a 6K byte read/write memory. Address bus 60 connects the digital memory 58 to the microprocessor 38, and data bus 62 connects the microprocessor 38 to the eight-bit digital-to-analogue converter 50, the eight-bit analogue-to-digital converter 44; the keypad 46; the single-digit LCD 48; and, the digital memory 58. The base station 20 provides a means for electrically connecting the portable pH data collection unit 10 to a personal computer 36 during the digital playback mode and to a strip chart 32 during the analogue playback mode. The strip chart connects via line 64 to the eight-bit digital-to-analogue converter 50. The personal computer 36 connects via line 66 to an RS-232 interface 52. A switch 38, located on the base station, communicates via line 68 to microprocessor 38 and enables the operator to select between the digital and analogue playback modes. A battery charger and power supply 70, contained within the base station 20, supplies power to the eight-bit digital-to-analogue converter 50 and to the nickel cadmium battery 54. The eight-bit digital-to-analogue converter 50 is only powered upon insertion into the base station 20, in order to conserve power.

The digital and analogue circuits utilize CMOS integrated technology to reduce power consumption. As mentioned previously, the nickel cadmium battery can be recharged in four hours for an additional 24 hours of remote data recording. If during operation a low voltage state is detected by the low voltage detector 56, the portable data collection unit is automatically put into a low power "idle" mode to preserve the data in the read/write memory. During the "idle" mode a "P" is displayed on the liquid crystal display 18. Insertion of the portable data collection unit 10 into the base station to recharge the batteries will cause the microprocessor to exit the "idle" state and enter the playback phase.

Microprocessor 38 performs calibration, data acquisition and compression, and data playback function in accordance with software stored in a 2K byte ROM 58. A flowchart of a software program is shown in FIGS. 5 through 10.

Figure 5:
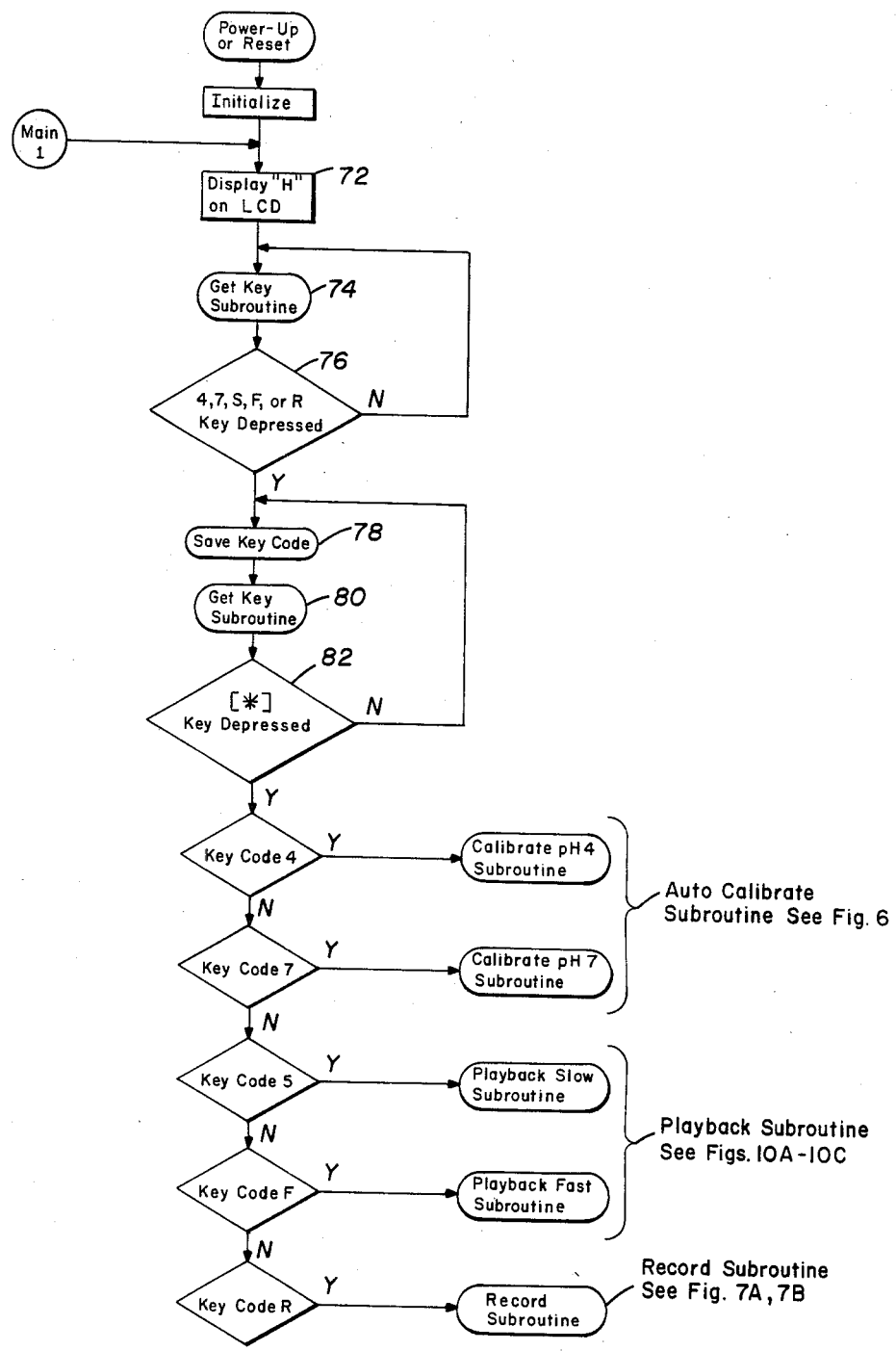
FIG. 5 is a flow chart illustrating the MAIN software routine.
Figure 6:
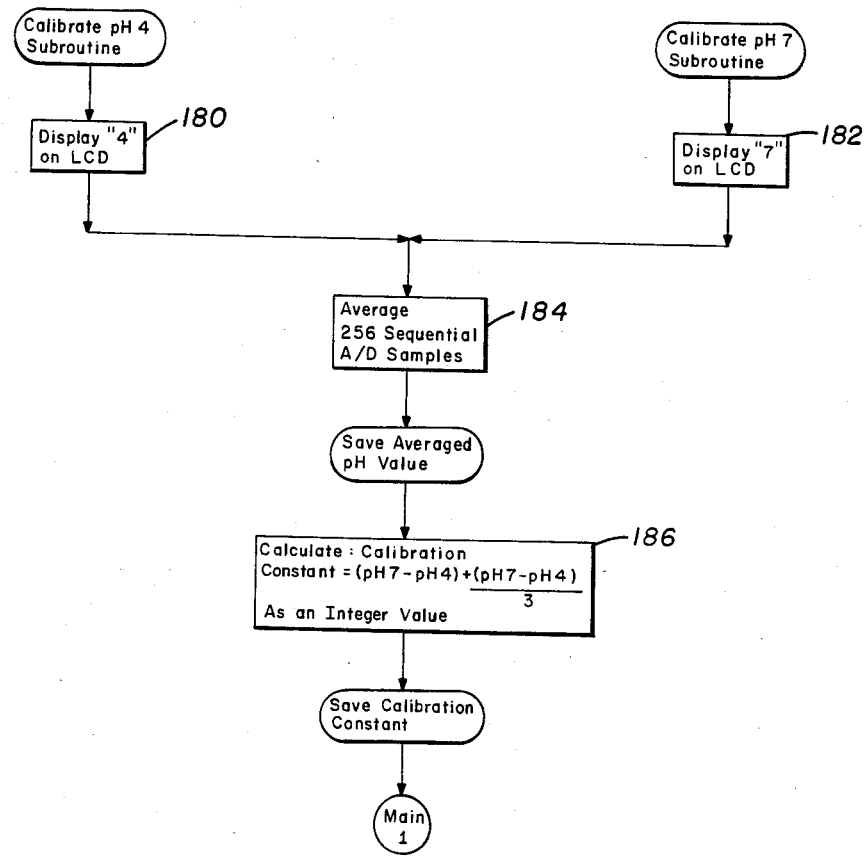
FIG. 6 is a flow chart illustrating the AUTO CALIBRATION subroutine.

The main routine shown in FIG. 5 performs initialization and selects a processing subroutine based on commands received via the keypad 16 (see FIG. 1). After being powered (or reset) and initialized, an "H" representing hold is displayed on the liquid crystal display (block 72). The program proceeds (at block 74) to call the GET KEY subroutine and determine whether a key has been pressed. If either the "7", "4", "S", "F" or "R" key has been pressed the program proceeds to block 78; if not, the program returns to block 74. If the appropriate key was pressed, the keycode data is saved (at block 78) and the GET KEY subroutine is again called. The program asks whether the [*] or ENTER KEY has been pressed (at Block 82). The program is designed so that the ENTER KEY [*] must be pressed after the function key in order for the program to branch into the designated processing subroutine. This feature prevents the patient from modifying the processing subroutine by inadvertently pressing a key. If the ENTER KEY [*] is not pressed the program returns to block 78; if, however, the ENTER KEY [*] is pressed the program proceeds to the process subroutine specified. If the "7" or "4" function key was pressed, the program branches to AUTO CALIBRATE subroutine (see FIG. 6); if the "S" or "F" function key was pressed, the program branches to the PLAYBACK subroutine (see FIG. 10A through 10C); if the "R" key is pressed, the program branches to RECORD subroutine (see FIG. 7A and B).

In addition to the processing subroutines, which shall be discussed in detail later in this application, there are two support subroutines: (1) the MEMCHECK subroutine (see FIG. 9), and (2) the WAIT group of subroutines, which includes the GET KEY subroutine, the OUTPUT subroutine, and the GET pH subroutine (see FIG. 8).

The MEMCHECK subroutine shown in FIG. 9 is called by the processing subroutine to advance the data table pointer (block 84) and check to see if the end of the data table has been reached. A flag (D =0) is set (block 86) to tell the calling routine when the end of the data table has been reached.

Figure 8:
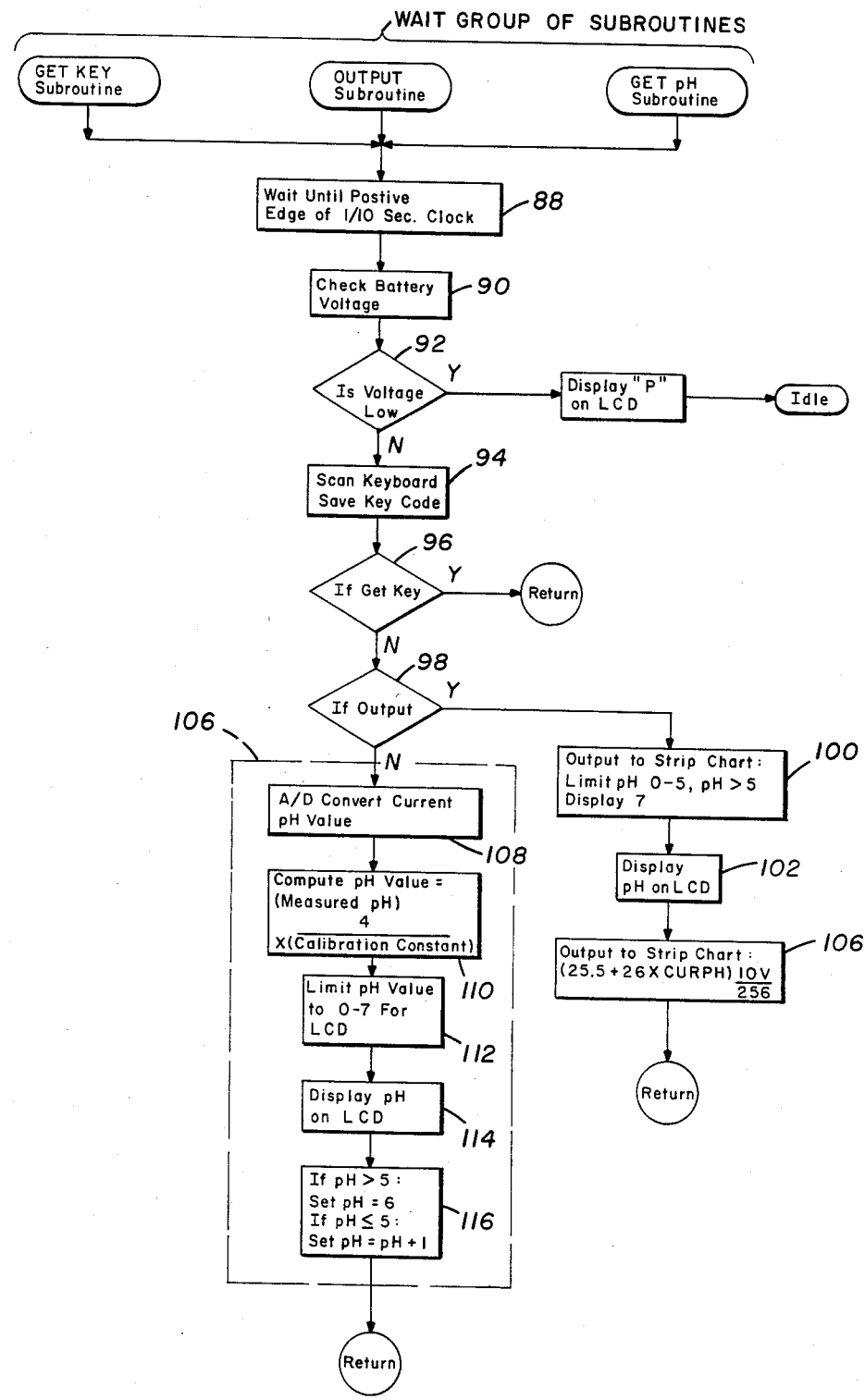
FIG. 8 is a flow chart illustrating the WAIT group of subroutines, which includes, GET KEY, OUTPUT and GET pH.
Figure 10B:
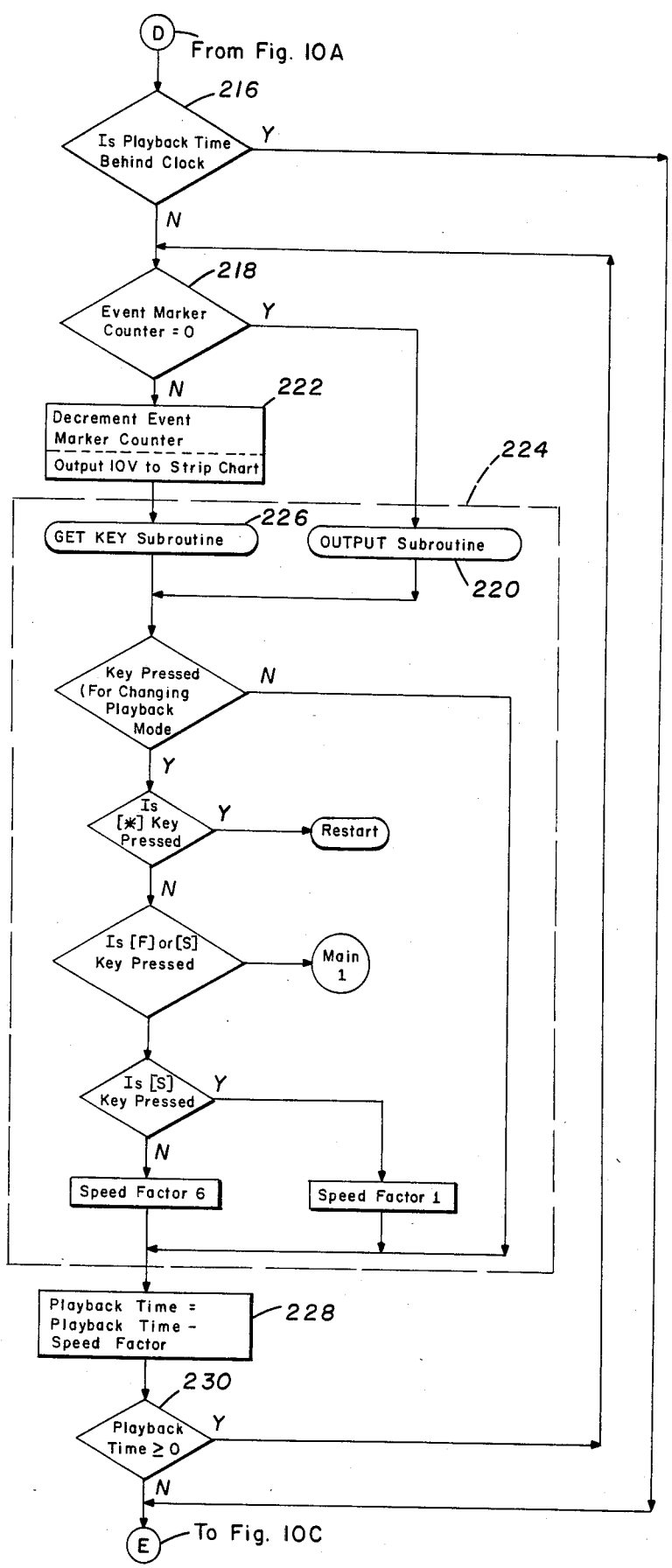
Figure 10C:
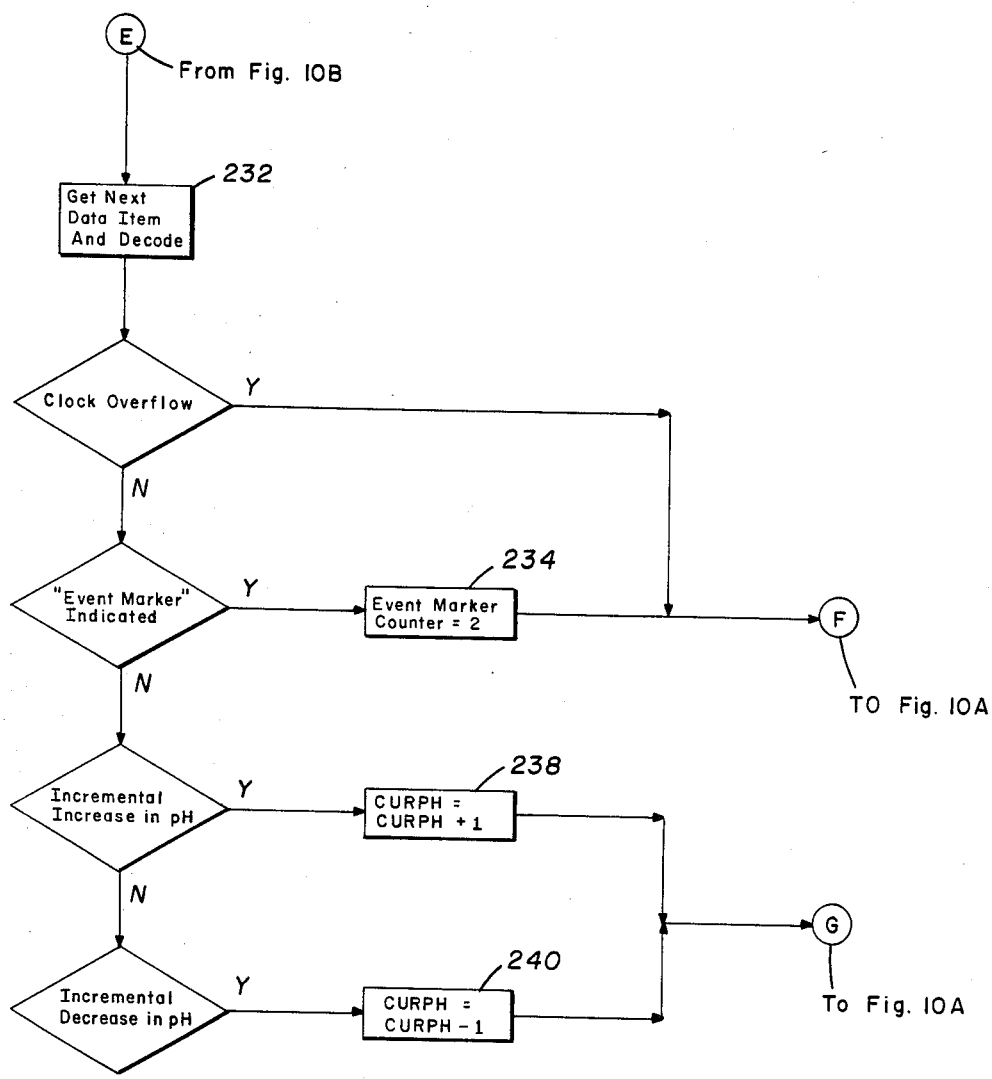

The WAIT subroutines shown in FIG. 8 are responsible for time delays, gathering pH and keycode data, and preparing an output signal when necessary to control a strip chart recorder. At block 88, the program performs a time delay and waits until the 1/10 clock second clock pulse goes high. This step assures that the program will loop through the specified processing subroutine once every 1/10 second. Next, the battery voltage is checked (block 90) and if the voltage is low the program branches to the "idle" state discussed earlier (block 92). Proceeding to block 94, the keypad is scanned, the keys are debounced, and the keycode data is saved. The program next branches into different paths depending on whether the processing subroutine requested GET KEY, OUTPUT or GET pH functions.

If GET KEY was requested, the program branches (at block 96) and returns to the processing subroutine with the keycode data.

If OUTPUT was requested, the program branches (at block 98) and calculates an output voltage level for the strip chart. If CURPH (the current pH integer) is greater than 5, it is scaled to 7 (at Block 100). (NOTE: In the preferred embodiment, it was felt that values from 0 to 5 pH were of medical interest. Any value greater than 5 pH is scaled to a 7 pH value to flag the physician that an excessive pH value was detected). The scaled pH value is then displayed on the liquid crystal display (block 102). At block 104, a calculation is made to determine an output voltage level corresponding to the current pH value (CURPH). That voltage will then be generated by the digital-to-analogue converter to drive the strip chart recorder.

If, however, GET pH was requested the program branches from block 98 directly to the GET pH subroutine 106. The program obtains a measured pH value from the analogue-to-digital converter (block 108) and scales the measured pH value (at block 110) using the "calibration constant" calculated by the AUTO CALIBRATION subroutine (see FIG. 6). The scaled pH value is calculated using the following formula:

$$pH = \text{measured pH} \times \left( \frac{4}{\text{"calibration constant"}} \right)$$

In the preferred embodiment the pH value may be further scaled to avoid loss of significance (i.e., the pH value may be multiplied by 8 to increase the number of significant bits). The program then limits the pH values from 0 to 7 (at block 112) and displays the pH value on the liquid crystal display (at block 114). At block 116 the CURPH value is determined by limiting and biasing the pH value as follows:

if pH >5 : set CURPH =6
if pH ≦5 : set CURPH =pH +1
(where CURPH is an integer value)

In the preferred embodiment the pH value was rounded to the next integer value to assist the physician in interpreting the pH data. However, other limits on rounding techniques are within the contemplation of the invention.

Data Acquisition and Compression Phase

Figure 7A:
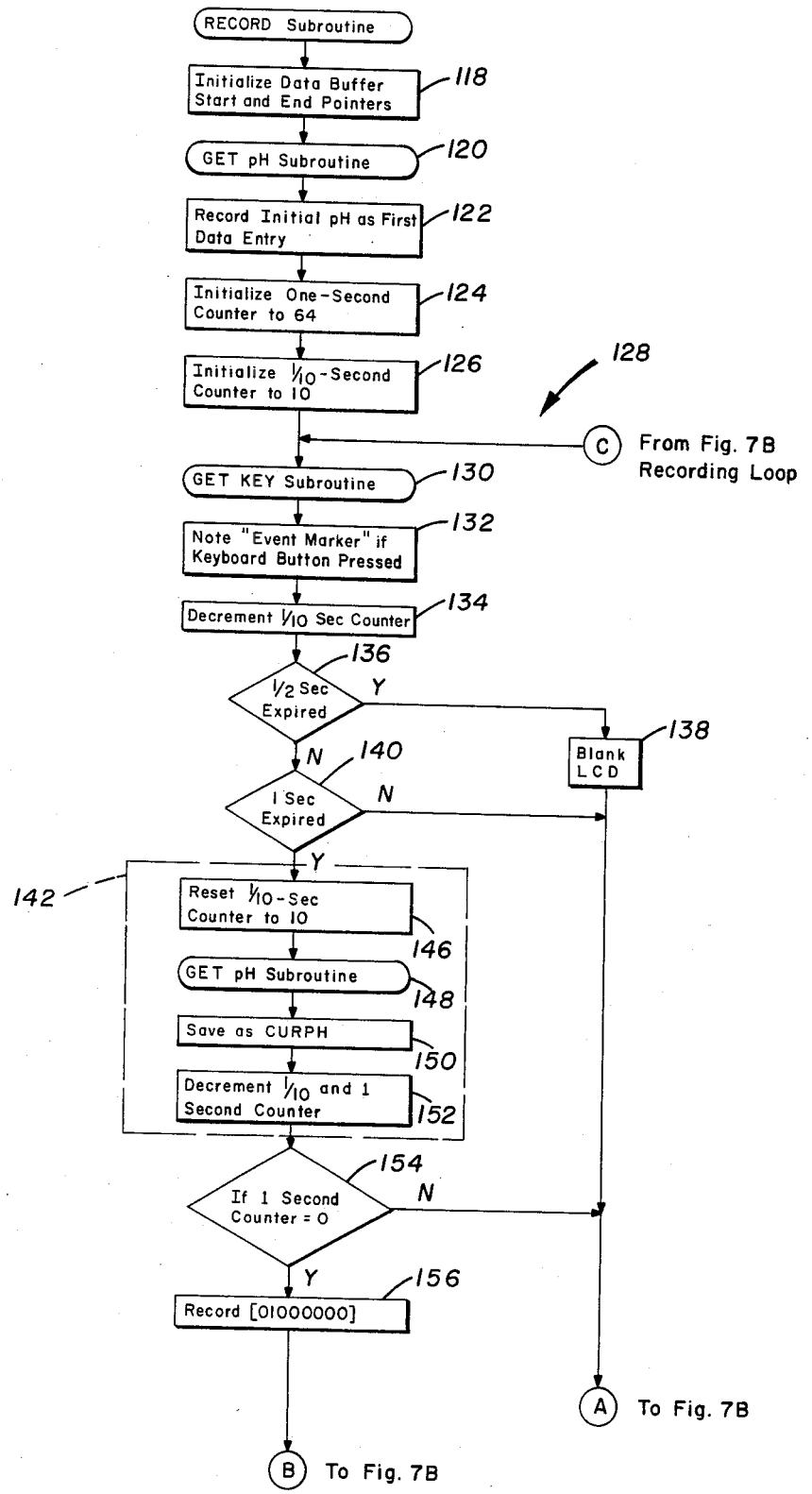
FIGS. 7A and 7B contain a flow chart illustrating the RECORD subroutine.
Figure 7B:
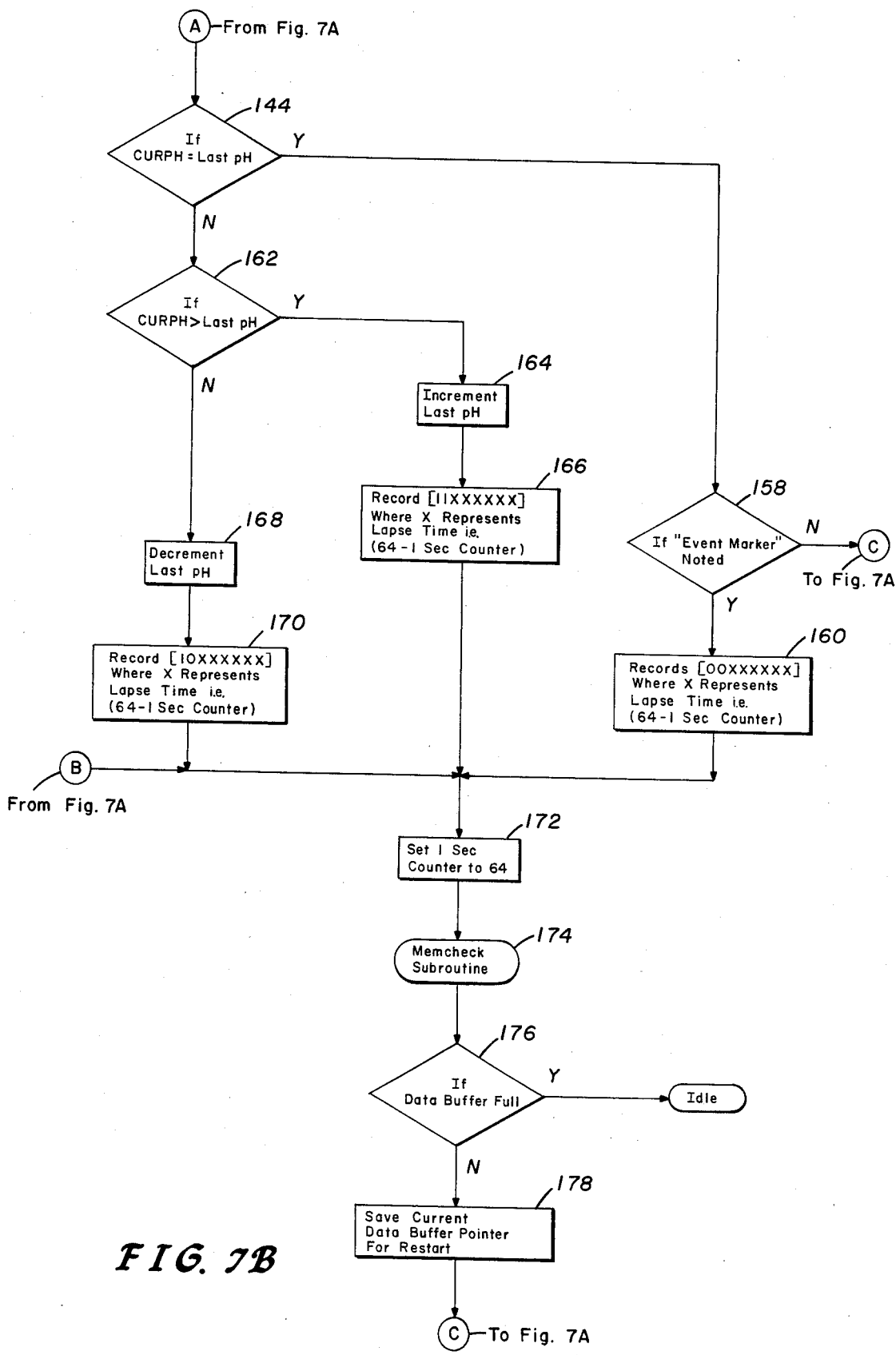

The RECORD subroutine, shown in FIGS. 7A and 7B, enables pH values to be determined once per second and "event marker" actuation to be sensed every 1/10 second. After data buffer start and end points have been initialized (block 118) the program calls the GET pH subroutine which calculates CURPH the current pH value (at block 120). The RECORD subroutine records as its initial data entry the first CURPH (at block 122) which will act as the last pH value during the first cycle through the recording loop. Proceeding to block 124 and 126, the one-second counter is initialized to sixty-four and the 1/10 second counter is initialized to ten.

The program now enters the "recording loop" 128 and records "events" associated with "event marker" actuation or with incremental changes in pH data. Proceeding to block 130, the program calls the GET KEY subroutine (see FIG. 8) to determine if the operator has pressed any of the appropriate keys. (NOTE: During processing of the "recording loop" actuation of any key will be interpreted an "event marker"). The patient will actuate an "event marker" in response to physical sensations the patient may experience. At block 134, the 1/10 second counter is decremented and if ½ second has elapsed since the last "event" the program branches (at block 136) and blanks the LCD display (at block 138). The LCD display is normally on, so a blank or pulse of the liquid crystal display (LCD) allows the patient or operator to know that the data recorder is operational. If ½ second has not elapsed since the last "event" the program asks whether one second has elapsed since the last event (at block 140). If one second has elapsed the program proceeds to that segment of the software 142 where CURPH data is gathered; if not, the program proceeds to block 144 (see FIG. 7B). Entering the CURPH gathering segment 142, the program resets the 1/10 second counter to 10 (at block 146) and calls the GET pH subroutine (at block 148). The pH value calculated in the GET pH subroutine (see FIG. 8) is saved as the CURPH value (block 150). The 1/10 and one second counters are decremented (block 152). The one-second counter is decremented since the CURPH data gathering segment occurs once per second and the 1/10 second counter is decremented to account for the time taken by the GET pH subroutine. Proceeding to block 154, the program determines if the one-second counter is zero, i.e., has sixty-four seconds elapsed since the last "event". (NOTE: An event can be either the actuation of an "event marker" by the patient or an incremental change in the sensed pH value). If 64 seconds have elapsed we proceed to block 156 and record the following 8-bit word: [01000000]. If 64 seconds have not elapsed we proceed to block 144 (see FIG. 7B).

At block 144, the CURPH value (which is the calibrated pH measured value) is compared with the LASTPH value. The initial LASTPH value is the initial pH value recorded previously in memory (see block 122, FIG. 7A). If CURPH equals the LASTPH value (i.e., if the pH value remains constant since the last "event", the program branches to block 158 and asks if an "event marker" was actuated. (NOTE: An "event marker" is saved at block 132 when any key is pressed by the patient.) If an "event marker" was not actuated the program loops back to block 130 (see FIG. 7A); if, however, an "event marker" was actuated, the program proceeds to block 160 and records the following 8-bit word: [00XXXXXX] where, bits 0 through 5 designated by the letter X, represent the elapsed time, i.e., sixty-four minus the value of the one-second counter, expressed in binary form.

Returning to block 144, if the CURPH value is different from the LASTPH value, the program determines whether this change is an increase in pH or a decrease in pH (at block 162). If the change represents an increase in pH the program proceeds to increment the LASTPH value (at block 164) and records the following 8-bit word (at block 166): [11XXXXXX], where bits 0 through 5, designated by the letter X, represent the elapsed time, i.e., sixty-four minutes the value of the one-second counter expressed in binary form. Similarly, if the change represents a decrease in pH, the program proceeds to decrease the LASTPH value (at block 168) and record the following 8-bit word (at block 170): [10XXXXXX] where, bits 0 through 5, designated by the letter X, represent the elapsed time (i.e., sixty-four minus the value of the one-second counter expressed in binary form).

It should be noted that the binary words recorded in memory at blocks 156, 160, 166 and 170 represent a significant compression of the continuous pH and time data. The data compression and selection technique described in this application is uniquely suited to monitor the episodic nature of the gastroesophageal reflux behavior. The CURPH value is a pH measurement taken once per second, scaled in accordance with calibration reference points and rounded to an integer value. The first entry recorded in memory is the actual pH value initially read by the probe and calibrated. For subsequent data points only an 8-bit word noting the occurrence of an "event" is recorded. If the CURPH integer differs from the LASTPH integer an "event" has occurred and the time of occurrence between the last recorded entry and the event is noted. In this manner the pH data compression technique reduces pH values and time data into a single 8-bit word recorded per "event". This technique reduces the number of recorded data points and also reduces the memory space necessitated for recording each data point.

After recording the 8-bit data word in memory (blocks 156, 160, 166 and 170) the program proceeds to block 172 and resets the one-second counter to sixty-four. The program next calls the MEMCHECK subroutine (see FIG. 9) which increments the data table pointer and sets a flag if the data table is full (at block 174). If MEMCHECK sets a flag indicating that the memory buffer is full, the program at block 176 branches into the "idle" state, where data are preserved until the program enters the playback mode. If the memory buffer is not full the program proceeds to save the current data for restart and returns to block 130 to again circulate through the "recording loop".

In operation, the program continously cycles through the "recording loop" checking for actuation of an "event marker" once every 1/10 second and checking for an incremental change in pH level once every second. The measured pH level is digitized and scaled automatically in accordance with a "calibration constant" calculated by the AUTO CALIBRATION subroutine (see FIG. 6) and is rounded to an integer value. If neither an "event marker" or an incremental change in the pH level is detected after 64 seconds, the program records a [01000000] and reinitializes the one-second counter. If an "event marker" is detected the program will record [00XXXXXX] where bits 0 through 5, designated by the letter X, represent the time elapsed from the last recorded entry. If an incremental change in pH is detected the program records [10XXXXXX] for an increase in pH or [11XXXXXX] for a decrease in pH, where bits 0 through 5, designated by the letter X, represent the time elapsed from the last recorded entry. After recording the 8-bit word associated with an "event marker" or an incremental pH change, the one-second counter is initialized and the program again recycles through the "recording loop". In this manner, the program continuously gathers and records data relevant to the patient's gastroesophageal reflux behavior.

Auto Calibration Phase

As mentioned previously, the signal appearing across the pH probe and the body potential electrode is digitized by an analogue-to-digital converter 44 once per second. The digital pH value is then automatically scaled in accordance with a "calibration constant". The program uses an AUTO CALIBRATION subroutine, shown in FIG. 6, to calculate the "calibration constant". As mentioned previously (see FIG. 3), the portable data collection unit is calibrated by attaching the body potential reference electrode 14 to the body of a patient and placing the pH probe 12 in a container holding a reference pH solution of pH 4 or pH 7. The solution can be placed in a conductive container and held by the patient during calibration, or the patient can touch a soaked gauze extending from the test tube containing the reference pH solution. The auto calibration subroutine is entered via the main routine (see FIG. 5) when the keycode corresponding to a "4" or "7" is actuated. The "4" key is pressed when the reference solution is at 4 pH and the "7" key is pressed when the solution is at 7 pH. Alternatively, with intraesophageal pH electrodes which contain an integral reference electrode, the combined electrode assembly is placed in the pH 4 and pH 7 reference solution and calibrated as described above.

Upon pressing the "4" or "7" key, followed by pressing the entry key [*], the program causes a "4" or a "7" to appear on the liquid crystal display (blocks 180 and 182). Proceeding to block 184 the program averages 256 sequential analogue-to-digital samples and saves the average pH sample. At block 186 the program calculates the "calibration constant" for an incremental change of 4 pH units. The "calibration constant" is calculated using the following formula:

$$\text{"calibration constant"} = (\text{pH7} - \text{pH4}) + \frac{(\text{pH7} - \text{pH4})}{3}$$

The integer value of the "calibration constant" is saved in memory and the program returns to the main routine (FIG. 5). In operation, the auto calibration subroutine will be used to calculate the "calibration constant" at least twice. The first iteration will calculate the constant using a reference solution of pH 4, and the second iteration will calculate the calibration constant using a reference solution of pH 7.

Playback Phase

After the portable data collection unit has been calibrated and has recorded up to 24 hours of data, the unit can be removed from the patient and plugged into the base station (see FIG. 2). The playback subroutine, illustrated in FIGS. 10A through 10C, reconstructs the compressed data as an analogue playback signal or transmits the data via an RS-232 bus to a remote computer. One enters the playback subroutine from the main computer (see FIG. 5) by pressing the "F" or "S" key followed by the enter key [*]. The "F" or "S" keys cause the analogue playback rate to be either ten or sixty times faster than normal (blocks 188, 190).

If the digital playback mode is requested by the appropriate positioning of switch 38 located on the base station, the program will branch from the analogue playback segment (at block 192) and output the memory data in binary form at 110 Baud (at block 194). The outputted binary data are sent via an RS-232 bus to a personal computer where the data can be processed, tabulated and displayed.

If an analogue output is required to drive a standard (0 to 10 volt) strip chart recorder, the program proceeds to reconstruct the data in an analogue format. The program retrieves from memory the first data item (at block 196). (NOTE: the first data item is the initial pH value which is not recorded in the compressed data format.) The first data item is saved as CURPH (at block 198). The data buffer is reviewed to see if the last data record has been read (blocks 200, 202, 204). If all data have been read, the program outputs zero pH and returns to the main routine (FIG. 5). If the memory contains additional data records the program retrieves the next 8-bit data word from memory (at block 206) and extracts elapsed time information from that data entry (at blocks 210 and 212). The playback time is then calculated and evluated to determine if the playback time exceeds the clock time—which can occur during the fast playback mode. If the playback time is not behind the clock and if the "event marker" counter flag is zero (block 218), the program calls the OUTPUT subroutine (at block 220). The OUTPUT subroutine causes the digital-to-analogue converter to provide the voltage level necessary to drive the strip chart, that voltage level corresponding to the CURPH value. If the "event marker" counter flag is not zero (block 218) the "event marker" counter is decremented, and ten volts are outputted to the strip chart (block 222). It will be noted later in the flow chart that the "event marker" counter is set equal to two when a data record indicates that an "event marker" was actuated by the patient. The playback subroutine will therefore generate a 10-volt driving signal during the two succeeding cycles through the playback loop.

At this point the program enters a segment of the routine 224 which scans the keypad for operator modifications to the playback mode. Both the OUPUT and GET KEY subroutines (blocks 220, 226) scan the keypad for the actuation keycode data. If the ENTER KEY [*] is pressed, the program is restarted and returns to the main routine (see FIG. 5) and initializes memory and data buffers. If the "F" or "S⇌" key is actuated, the program will correspondingly reset the speed factor for fast or slow playback. In this manner, the physician can speed up or slow down the data display on the strip chart at any time, or any number of times, during the data playback mode. Proceeding through the playback loop the playback time is adjusted to account for the possible change in speed factor. If the playback time is greater than zero, the program loops back to block 218.

If, however, the playback time is behind the clock, the program proceeds to get the next 8-bit data word (at block 232). If the 8-bit data word records an "event marker" actuation, the event counter is set equal to two (at block 234) and the program loops back to block 200 (see FIG. 10A) to process that data. (NOTE: Setting the event counter equal to two causes an output of ten volts to be sent to the strip chart recorder for the next two succeeding cycles through the playback loop (see blocks 218, 222).

If, however, a positive incremental change in pH is indicated by the next data word (i.e., if the two most significant bits are [1,1]) the program increments the CURPH value (at block 238) and recycles through the playback loop indicating the appropriate output voltage to be generated and sent to the strip chart. Similarly, if a negative incremental change in pH is indicated by the next 8-bit data word (i.e., if the two most significant bits are [1,0]) the program decreases the CURPH value (at block 240) and recycles through the playback loop. In this manner, the 8-bit data words are reconstructed into an analogue signal which can drive a strip chart.

It is to be understood that the data construction technique illustrated in the preferred embodiment could be modified to drive various forms of strip charts or analogue recording devices and is not limited to a (zero to ten volt) strip chart recorder. Similarly, it is to be understood that the digital playback mode can use similar techniques to retrieve actual pH data and time information from the compressed data. It is envisioned that the personal computer which received the digital data via an RS-232 bus will use the technique to display the data graphically, and use similar data analysis techniques to tabulate data relevant to gastroesophageal reflux episodes. It is also to be understood that the invented data compression technique has generalized application in recording physiological data which is "bursty" and not periodic in nature. Such physiological data are characterized by bursts of activity separated by periods of quiescence or low levels of activity.

Obviously many modifications and variations of the invention are possible in light of the above teachings. It is therefore to be understood that within the scope of the appended claims the invention may be practiced otherwise than as specifically described.

What is claimed and desired to be secured by Letters Patent of the United States is:

1. A physiological data collector for recording physiological data characterized by bursts of rapid activity interspersed among relatively long periods during which there is little or no activity, said physiological data collector comprising:
   a data collection means for periodically measuring and digitizing physiological data;
   a means for setting a reference value equal to an initial measured value of said physiological data and for recording as a data entry said initial measured value;
   a data reduction means for comparing a current measured physiological data value with said reference value, for recording an event in memory when there is a difference between said current measured physiological data value, and said reference value at least equal to a preselected incremental amount, wherein a data entry corresponding to said event includes elapsed time since the last recorded data entry and a tag indicating whether there is a positive or negative change and, for increasing or decreasing said reference value by said preselected incremental amount, as indicated by said tag; and,
   a means for recording a data entry in memory and reinitializing elapsed time when a data entry has not been recorded within a certain maximum time elapsed.

2. The apparatus of claim 1, wherein said data entry corresponding to an event is a (n+m) bit word, with the least significant m bits storing time elapsed since the last recorded data entry and the most significant n bits storing tag information.

3. The apparatus of claim 2, wherein said maximum time elapsed is equal to $2^{m+1}$ data collection cycles of said data collection means.

4. The apparatus of claim 2, wherein said means for recording a data entry in memory when a data entry has not been recorded within said certain maximum time elapsed is [01000000] and wherein said maximum time elapsed in 64 seconds.

5. The apparatus of claim 1, wherein said data entry is an 8-bit word with [10XXXXXX] recorded for an increase in said current measured physiological data value at least equal to said preselected incremental amount above said reference value and [11XXXXXX] recorded for a decrease in said current measured physiological data value at least equal to said preselected incremental amount below said reference value where bits designated by the letter X represent the elapsed time from the last recorded data entry.

6. A portable pH data collector, comprising:
a data collection means for periodically measuring and digitizing pH values;
a means for setting a reference pH value equal to an initial pH value and for recording as a data entry said initial pH value;
a data reduction means for comparing a measured pH value with the reference pH value, for recording an event in memory when there is a difference between said measured pH value and said reference pH value at least equal to a preselected incremental amount, wherein a data entry corresponding to said event includes elapsed time since the last recorded data entry and a tag indicating whether there is a positive or negative change and, for increasing or decreasing said reference pH value by said preselected incremental amount, as indicated by said tag; and,
a means for recording a data entry in memory and reinitializing elapsed time when a data entry has not been recorded within a certain maximum time elapsed.

7. The apparatus of claim 6, further comprising:
a keypad associated with said portable pH data collector having at least one key;
a means for periodically scanning said keypad and for actuating an event marker when a key has been pressed; and,
a means for recording an event in memory when said event marker is actuated, wherein a data entry corresponding to said event marker includes elapsed time since the last recorded data entry and a tag indicating an event marker was actuated.

8. The apparatus of claim 7, further comprising:
an auto calibration means for generating a calibration constant when a pH probe associated with said portable pH data collector is brought in association with solutions of reference pH levels and a body reference electrode is brought in association with a patient's body; and,
a means for scaling said pH value measured by said data collection means in accordance with said calibration constant.

9. The apparatus of claim 8, further comprising:
a playback means for reconstructing data entries and for generating an analog signal in accordance with said reconstructed data, said analog signal driving a strip chart recorder.

10. The apparatus of claim 8, further comprising:
a playback means for reconstructing data items and for transmitting said data in binary form to a computer for processing.

11. The apparatus of claim 7, wherein said data entry corresponding to said event marker is the following 8-bit word [00XXXXXX] where bits designated by the letter X represent elapsed time from the last recorded data entry.

12. The apparatus of claim 11, wherein said means for scanning said keypad scans once every 1/10th second and wherein said elapsed time is measured in seconds.

13. The apparatus of claim 6, wherein said data entry is an 8-bit word with [10XXXXXX] recorded for an increase in pH at least equal to said preselected incremental amount above said reference pH value and [11XXXXXX] recorded for an decrease in pH at least equal to said preselected incremental amount below said reference pH value, where bits designated by the letter X represent the elapsed time from the last recorded data entry.

14. The apparatus of claim 13, wherein said data collection means measures the digitized pH values once per second, and said elapsed time is measured in seconds.

15. The apparatus of claim 13, wherein said means for recording a data entry in memory when a data entry has not been recorded within a certain maximum time elapsed is [01000000] and wherein said maximum time elapsed is 64 seconds.

16. The apparatus of claim 6, wherein said data entry corresponding to an event is a (n+m) bit word, with the least significant m bits storing time elapsed since the last recorded data entry and the most significant n bits storing tag information.

17. The apparatus of claim 16, wherein said maximum time elapsed is equal to $2^{m+1}$ data collection cycles of said data collection means.

18. A portable pH data collector for measuring pH within a patient's body by inserting a pH probe into the patient's body and attaching a body reference electrode in association with said patient's body, said body reference electrode either attached to said body surface or placed into said body in combination with said pH probe, said portable pH data collector, comprising:
an analog to digital converter connected to said pH probe and said body reference electrode for providing digital values of measured pH;
a memory for storing data entries and for storing a software routine; and, a microprocessor for providing control, calibration, data acquisition and compression, and data playback functions, wherein said microprocessor is coupled to said analog to digital converter and said memory via a data bus, and wherein said memory is also connected to said microprocessor via an address bus, and wherein said microprocessor further comprising,
an acquiring means for periodically acquiring digital pH values from said analog to digital converter;
a storage means for recording in said memory a data entry corresponding to the initial pH value and for setting a reference pH value equal to said initial pH value;

a data reducing means for comparing the current digitized pH value with the reference pH value, recording a data entry in memory when there is a difference between said current digitized pH value and said reference value at least equal to a preselected incremental amount, wherein a data entry corresponding to said incremental change in pH includes the time elapsed since the last recorded data entry and a tag indicating whether there is a positive or negative change and, for increasing or decreasing said reference pH value by said preselected incremental amount, as indicated by said tag; and, a recording means for recording a data entry in memory and reinitializing elapsed time when a data entry has not been recorded within a certain maximum elapsed time.

19. The apparatus of claim 18, further comprising a keypad having at least one key, wherein said keypad is connected via said data bus to said microprocessor, and wherein said microprocessor further includes: a scanning means for scanning the keypad periodically for key actuations; and, a means for noting an event marker if a key was actuated and recording in said memory a data entry indicating elapsed time since the last recorded data entry and a tag designating event marker actuation.

20. The apparatus of claim 19, wherein said microprocessor further includes:

a calibration means for calibrating said pH probe for said patient, wherein said body reference electrode is attached to said patient's body and wherein said pH probe is placed in a reference solution of known pH level and wherein said reference pH solution is in electrical communication with said patient's body; and, a scaling means for scaling each of said digitized pH values in accordance with said calibration constant.

21. The apparatus of claim 20 further comprising a digital to analog converter connected via said data bus to said microprocessor for generating an output voltage sufficient to drive a strip chart recorder, and wherein said microprocessor further includes a means for reconstructing said data entries in memory and controlling said digital to analog converter so as to generate an analog signal in accordance with said reconstructed data to drive a strip chart recorder.

22. The apparatus of claim 20, further comprising an RS-232 interface operably connected to said microprocessor for transferring data to a remote computer for processing, and wherein said microprocessor further includes a means for retrieving and transmitting data entries to said remote computer via said RS-232 interface.

23. The apparatus of claim 22, wherein said remote computer processes the transmitted data entry and tabulates data relative to gastroesophageal reflux episodes.

24. The apparatus of claim 22, wherein said portable pH data collector comprises a portable data collection unit for pH data acquisition, compression and recording, and a base station for recharging said portable data collection unit when said base station is electrically coupled to said portable pH data collection unit, and wherein said electrical coupling is possible only after said pH electrode and said body reference electrode are disconnected from said portable pH data collector.

25. The apparatus of claim 19, further comprising a display connected by said data bus to said microprocessor for displaying at least one character, and wherein said microprocessor further includes a means for displaying said digitized pH values on said display.

26. The apparatus of claim 19, further comprising a low voltage detector for alerting said microprocessor when a battery supplying voltage to said portable pH data collector is supplying low voltage, and wherein said microprocessor further includes an idle state means for preserving data entries in memory while said battery voltage is low.

* * * * *